United States Patent [19]

Brunke et al.

[11] Patent Number: 4,912,088
[45] Date of Patent: Mar. 27, 1990

[54] USE OF CAMPHOLENENITRILES AS FRAGRANCE

[75] Inventors: Ernst-Joachim Brunke; Claus-Hermann Kappey, both of Holzminden, Fed. Rep. of Germany

[73] Assignee: Draggo Gerberding & Co., Holzminden, Fed. Rep. of Germany

[21] Appl. No.: 229,619

[22] Filed: Aug. 5, 1988

[30] Foreign Application Priority Data

Aug. 7, 1987 [DE] Fed. Rep. of Germany ....... 3726418

[51] Int. Cl.$^4$ ............................................. A61K 7/46
[52] U.S. Cl. .................................................... 512/6
[58] Field of Search ........................... 512/2,6; 558/432

[56] References Cited

U.S. PATENT DOCUMENTS 3,981,891  9/1976  Celli et al. ........................... 558/432
4,456,561  6/1981  Lenselink ............................... 512/6
4,490,284  12/1984  Brunke et al. ......................... 512/6

FOREIGN PATENT DOCUMENTS 2053199  2/1981  United Kingdom ................ 558/432

*Primary Examiner*—James H. Reamer
*Attorney, Agent, or Firm*—Zarley McKee, Thomte, Voorhees & Sease

[57] ABSTRACT

It has been found that α-campholenenitrile with formula A and γ-campholenenitrile with formula B

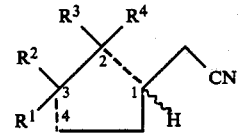

A: $\Delta^{3\,(4)}$; $R^1 = H$, $R^2 = R^3 = R^4 = CH_3$
B: $\Delta^{1\,(2)}$; $R^1 = R^2 = R^3 = CH_3$, $R^4 = H$ are excellent for use as fragrances, especially as components of fragrance mixtures for perfuming cosmetics or other consumer goods. The two nitriles can be used individually or in mixture with each other.

5 Claims, No Drawings

USE OF CAMPHOLENENITRILES AS FRAGRANCE

Compounds with a campholene structure occur naturally as components of essential oils, e.g., α-campholene aldehyde 2 in juniperberry oil (A. F. Thomas, Helv. Chim. Acta, Vol. 55, 1972, p. 815). α-Campholene aldehyde has a fresh resinous odor.

Some derivatives of campholene aldehyde 2 with a lengthened side chain have odors suggesting a woody, animal type corrresponding to certain aspects of East Indian sandalwood oil (survey in E.-J. Brunke and E. Klein "Chemistry of Sandalwood Fragrance," in "Fragrance Chemistry" (editor E. Theimer), Academic Press, New York, 1982, p. 424–426)).

2

In general, there is a constant demand for synthetic fragrances that can be produced to advantage with a uniform quality, remain stable in prolonged storage even in contact with other substances and have desired olfactory properties, i.e., pleasant fragrances that are as natural as possible, are of adqeuate intensity and are capable of having a positive influence on the fragrance of cosmetics or other consumer commodities. It has been found that α-campholenenitrile of general formula A and γ-campholenetrile of general formula B satisfy this requirement in an excellent manner, because they can be produced with no problem, are extremely stable compounds with a highly individual fragrance characteristic and strong radiant emission and are fragrances that have a variety of uses. Due to their fragrance properties, they can be used as components of perfume oils of a wide variety of odor directions to enrich creative perfumery. Due to their high chemical stability, especially their resistance to acids, they can also be used to advantage to perfume relatively aggressive basic compositions (detergents, household cleaners, etc.).

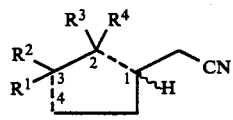

A: $\Delta^{3(4)}$; $R^1 = H$, $R^2 = R^3 = R^4 = CH_3$

B: $\Delta^{1(2)}$; $R^1 = R^2 = R^3 = CH_3$, $R^4 = H$

This invention therefore concerns the use of α-campholenenitrile with general formula A (also designated below as 4) as well as γ-campholenenitrile with general formula B (also designated below as 6) as perfumes or as components of perfume mixtures for perfuming cosmetic or other consumer commodities. General formulas A and B also include the stereoisomeric forms of campholenenitriles such as those indicated by the zigzag line. Both nitriles A and B can be used in pure form as as a mixture according to this invention.

Nitrile A which corresponds to campholene aldehyde 2 had already been synthesized in 1883 by V. Meyer by action of methyl chloride on camphor oxime. However, at that time the structure of the product was not yet known (V. Meyer, Ber. Dt. Chem. Ges., Vol. 16, 1883, p. 2981). F. Tiemann succeeded in elucidating the structure and assigning formula A to it (F. Tiemann, Ber. Dt. Chem. Ges., Vol. 29, 1896, p. 3006). In the same article this author describes the synthesis of A by the action of dilute sulfuric acid on camphor oxime. Pyrolysis or photolysis of camphor oxime also yields nitrile A (T. Sato and H. Obase, Tetrahedron Letters, 1967, 1633–1636). In addition, A has also been obtained from camphor oxime by the action of phosphorus pentoxide (M. Nazir et al., Pakistan Journal of Science and Industrial Research, Vol. 10, No. 1, 1967, p. 13–16) or concentrated hydrochloric acid (N. G. Kozlov and T. Pekh, Zh. Org. Khim., 1982, 18(5), 1118–1119). A was likewise identified in the reaction mixture of photolysis or pyrolysis of camphor nitrimine (L. J. Winters, J. F. Fisher and E. R. Ryan, Tetrahedron Letters, 1971, p. 129–132).

The literature does not contain any information on the olfactory properties of α-campholenylnitrile A, and γ-campholenenitrile B is not yet described in the literature at all.

In an appraisal of the fragrance, pure α-campholenenitrile A has a strongly radiant, fruity and sweet, spicy aroma in the direction of tonka extract and citrus peel with aspects of orris root extract, whereas pure γ-campholenenitrile B has a strong radiant fragrance with a spicy and fresh woody effect and a secondary aspect in the direction of cumin. Both campholenenitriles enhance the head notes and radiation of perfume oils.

The fragrance effects of campholenetriles A and B are original and novel with respect to the pure components and also with respect to mixture thereof. Furthermore, these fragrance effects are surprising in that they clearly differ from the olfactory properties of known campholene derivatives on the one hand and on the other hand they could not have been foreseen from the fragrance properties of other known nitriles. The relatively strong metallic, fatty secondary notes which are undesirable but typical of known aliphatic nitriles such ad decylnitrile, tridecene-2-nitrile, citronellylnitrile or geranylnitrile with citrus main notes do not occur with nitriles A and B. Furthermore, the general experience that the olfactory properties of known fragrances do not permit any compelling inferences regarding the properties of structurally related compounds is also confirmed here because neither the mechanism of fragrance perception nor the influence of chemical structure on fragrance perception have been adequately researched and thus it is not normally possible to preduct whether a modified structure of known perfumes will lead to a change in olfactory properties at all and whether these changes are to be evaluated positively or negatively.

To produce nitriles A and B, the procedure followed may be different. Two alternative reaction pathways have proven especially expedient, namely:

1. Oximation of campholene aldehyde 2 and subsequent dehydration according to the following scheme I:

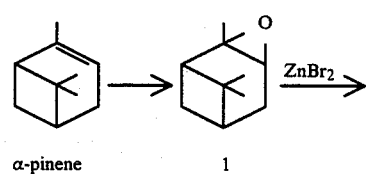

α-pinene     1

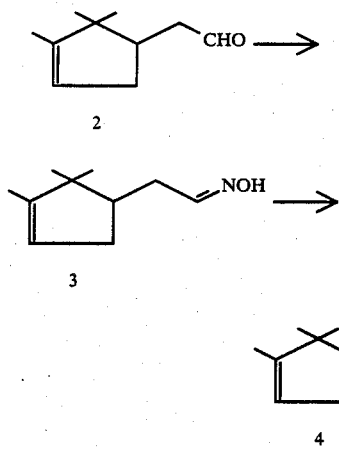

Starting from α-campholene aldehyde 2, the rearrangement product of α-pinene epoxide, the corresponding oxime 3 was synthesized by conventional methods and dehydrated with acetic anhydride to form pure α-campholenenitrile 4 (A).

2. Rearrangement of camphor oxime 5 according to the following scheme II.

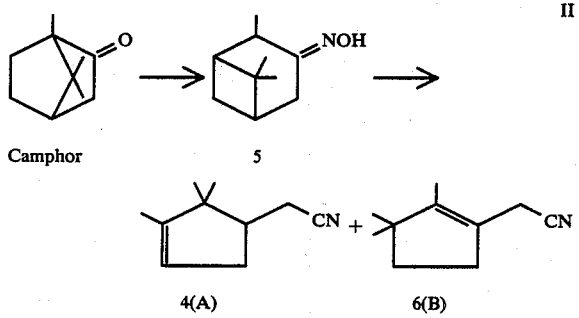

Oxime 5 produced from camphor according to conventional methods was reacted with dilute sulfuric acid according to the procedure described by Tiemann. First a mixture of α-campholenenitrile 4 and α-campholenenitrile 6 was formed. By reacting with sulfuric acid for several hours, a practically complete conversion of α-campholenenitrile to γ-campholenenitrile was achieved. Thus pure γ-campholenenitrile 6 (B) was obtained for the first time.

Independently of the reaction pathway proposed, both nitriles A and B can be produced either as optically active or inactive products starting from optically active or inactive educts, and the pure stereoisomers as well as their mixtures and racemates can also be used according to this invention.

The following examples are presented to illustrate this invention without limiting it.

EXAMPLE 1

| Perfume oil with a sweetish herbal note | a | b |
|---|---|---|
| Orange oil | 180 g | 180 g |
| Isobornyl acetate | 300 g | 300 g |
| Cyclogalbanate | 5 g | 5 g |
| Oil of bergamot | 100 g | 100 g |
| Oil of rosemary, Tunisian | 30 g | 30 g |
| Oil of mugwort | 1 g | 10 g |
| Base Bigaradia 18* | 15 g | 15 g |
| Apple base* | 10 g | 10 g |
| Dimethyltetrahydrobenzaldehyde | 5 g | 5 g |
| Styrolyl acetate | 20 g | 20 g |
| Hexyl cinnamaldehyde, alpha | 100 g | 100 g |
| Oil of geranium, Bourbon, synthetic | 10 g | 10 g |
| Phenethyl alcohol | 30 g | 30 g |
| Citronellol | 100 g | 100 g |
| Ylanate (p-tert-butylcyclohexyl acetate) | 30 g | 30 g |
| Lignofix* (acetylcedrene) | 30 g | 30 g |
| Oil of patchouli | 20 g | 20 g |
| Stemone (Givaudan) | 5 g | 5 g |
| Galbanum resinoid | 10 g | 10 g |
| Musk, Ambrette | 20 g | 20 g |
| Cyclopentadecanolide | 20 g | 20 g |
| α-Campholenenitrile | — g | 30 g |
| Dipropylene glycol | 30 g | — g |
| | 1080 g | 1080 g |

*Special product of DRAGOCO

Perfume oil a has a sweetish herbal note.

Composition b, which contains about 3% α-campholenenitrile instead of dipropylene glycol which has a neutral odor, has a powerful fresh fragrance and an interesting hint of fruity tone. It is very suitable for bubble baths.

EXAMPLE 2

| Perfume oil with a spicy woody character | a | b |
|---|---|---|
| Evernyl ® | 5 g | 5 g |
| Brahmanol ® (DRAGOCO) | 5 g | 5 g |
| Eugenol methyl ether | 5 g | 5 g |
| Decatone ® (Givaudan) 10% in DPG | 5 g | 5 g |
| Galaxolide ® (IFF) | 20 g | 20 g |
| Nutmeg oil | 20 g | 20 g |
| Lilial ® | 30 g | 30 g |
| Sauge Claree resinoid | 35 g | 35 g |
| Oak moss extract, green, Yugoslavian (50% in DPG) | 50 g | 50 g |
| Isobutyl quinoline (10% in DPG) | 50 g | 50 g |
| Musk ketone | 60 g | 60 g |
| Eugenol | 80 g | 80 g |
| Linalyl acetate | 100 g | 100 g |
| Lavandin oil | 100 g | 100 g |
| Oil of bergamot (free of furocoumarin) | 100 g | 100 g |
| Lignofix (DRAGOCO) | 290 g | 290 g |
| Dipropylene glycol | 45 g | — |
| γ-Campholene nitrile | — | 45 g |
| | 1000 g | 1000 g |

Composition a has a powerful spicy, woody aroma whereas when γ-campholenenitrile is added, composition b has a highly desirable hint of sweetish herbal notes (in the direction of lavender) as well as a definite roundness.

EXAMPLE 3

| Perfume oil with an herbal note | a | b |
|---|---|---|
| Oil of bergamot | 100 g | 100 g |
| Oil of cedar leaf | 150 g | 150 g |
| Oil of wormwood | 30 g | 30 g |
| Oil of rosemary, Tunisian | 45 g | 45 g |
| Oil of spike, Spanish | 20 g | 20 g |
| Oil of clary | 10 g | 10 g |
| Peppermint oil, Brazilian | 5 g | 5 g |
| Phenethyl alcohol | 100 g | 100 g |

| -continued | | |
|---|---|---|
| Perfume oil with an herbal note | | |
| | a | b |
| Citronellol | 30 g | 30 g |
| Diphenyl ether | 10 g | 10 g |
| Oil of geranium, Bourbon | 5 g | 5 g |
| Linalool | 50 g | 50 g |
| Linalyl acetate | 60 g | 60 g |
| Methylionone, gamma | 50 g | 50 g |
| Ylanate (4-tert-butylcyclohexyl acetate) | 50 g | 50 g |
| Terpineol, pure | 100 g | 100 g |
| Anisaldehyde | 50 g | 50 g |
| Lignofix* (acetylcedrene) | 100 g | 100 g |
| Benzyl salicylate | 50 g | 50 g |
| Amyl salicylate | 70 g | 70 g |
| Ylang-ylang oil, synthetic | 30 g | 30 g |
| Galbanum extract | 5 g | 5 g |
| Coumarin | 50 g | 50 g |
| Cyclopentadecanolide | 30 g | 30 g |
| Dipropylene glycol | 40 g | — |
| γ-Campholenenitrile | — | 40 g |
| | 1240 g | 1240 g |

*Special product of DRAGOCO

Perfume oil a has an herbal fragrance complex.

Composition b, which contains about 3% γ-campholenenitrile, has a stronger effect, emphasizes the herbal note and is characterized by a novel tea aspect.

EXAMPLE 4

| Perfume oil of a floral type | | |
|---|---|---|
| | a | b |
| Brahmanol ® | 20 g | 20 g |
| Citronellol | 50 g | 50 g |
| Phenethyl alcohol | 175 g | 175 g |
| Indole | 4 g | 4 g |
| Isoeugenol | 6 g | 6 g |
| Benzyl acetate | 30 g | 30 g |
| Linalool | 40 g | 40 g |
| Terpineol, pure | 240 g | 240 g |
| Muguet alcohol* (2,2-dimethyl-3-phenylpropanol) | 200 g | 200 g |
| Cinnamic alcohol | 40 g | 40 g |
| Citronellyl acetate | 20 g | 20 g |
| Frambinon* | 15 g | 15 g |
| Buccoxime* (1,5-dimethyl-8-hydroxyiminobicyclo[3.2.1]octane) | 70 g | 70 g |
| Dipropylene glycol | 90 g | 87 g |
| α-Campholenenitrile (A) | — | 2 g |
| γ-Campholenenitrile (B) | — | 1 g |
| | 1000 g | 1000 g |

*Special product of DRAGOCO

Composition a has a powerful, gently floral note in the direction of lily of the valley with an exotic fruity undertone. Adding small amounts of compounds A and B (composition b) yields a completely different fragrance characteristic in the interesting direction of "white flowers" with "Chypre" aspects.

EXAMPLE 5

The following table illustrates the extremely high stability of α-campholenenitrile in various basic compositions (in which γ-campholenenitrile can be used similarly). Of the three ratings shown here for stability, mainly "very good" occurs and there is only one "good." Not a single rating of "not good" was obtained.

| | | Fragrance stability | | | | |
|---|---|---|---|---|---|---|
| Test base | Dosage | 1 month at room temperature | 1 month at 40° C. | 3 months at room temperature | 3 months at 40° C. | Fragrance effect (covering the perfume base, radiant effect) |
| Acidic cleaner (H₃PO₄) | 0,5 | SG | SG | SG | G | strong |
| Alkaline cleaner | 0,5 | SG | SG | SG | SG | strong |
| Soap, white | 1,0 | SG | SG | SG | SG | strong |
| All-purpose detergent with TAED | 0,2 | SG | SG | SG | SG | very strong |
| All-purpose detergent, liquid | 0,3 | SG | SG | SG | SG | strong |
| Laundry softener | 0,2 | SG | SG | SG | SG | very strong |
| Bubble bath | 3,0 | SG | SG | SG | SG | very strong |
| Shampoo | 0,5 | SG | SG | SG | SG | very strong |
| Aerosol antiperspirant | 4,0 | SG | SG | SG | SG | strong |
| Spray deodorant | 1,0 | SG | SG | SG | SG | strong |
| Vanishing cream, oil/water emulsion | 0,3 | SG | SG | SG | SG | very strong |

Stability:
SG = very good (no change in note)
G = good (minor change in note, acceptable)
NG = not good (change in note, not acceptable)

We claim:

1. A method of enhancing fragrance of substances, said method comprising adding a small but fragrance enhancing effective amount of a campholenenitrile selected from the group of campholenenitriles of the formula (A) and of the formula (B) below:

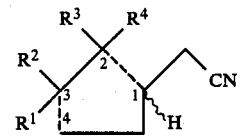

A: $\Delta^{3\,(4)}$; $R^1 = H$, $R^2 = R^3 = R^4 = CH_3$
B: $\Delta^{1\,(2)}$; $R^1 = R^2 = R^3 = CH_3$, $R^4 = H$ wherein for formula (A) $R^1$ equals hydrogen, $R^2$, $R^3$ and $R^4$ equal methyl, and for formula (B) $R^1$, $R^2$ and $R^3$ equal methyl and $R^4$ equals hydrogen.

2. The method of claim 1 wherein said campholenenitrile is α-campholenenitrile.

3. The method of claim 1 wherein said campholenenitrile is γ-campholenenitrile.

4. The method of claim 1 wherein said campholenenitrile is a mixture of α-campholenenitrile and γ-campholenenitrile which has a content of from 0.5% to 99.5% of α-campholenenitrile and from 99.5% to 0.5% γ-campholenenitrile.

5. A cosmetic fragrance composition which comprises a fragrance carrier and a small but fragrance enhancing effective amount of a campholenenitrile selected from the group consisting of α-campholenenitrile and γ-campholenenitrile or mixtures thereof.

* * * * *